United States Patent [19]

Hui et al.

[11] Patent Number: 4,897,500

[45] Date of Patent: Jan. 30, 1990

[54] METHOD OF DEACTIVATING RESIDUES OF THE PRODUCTION OF DIMETHYLALUMINUM HYDRIDE AND DIMETHYLGALLIUM HYDRIDE

[75] Inventors: Benjamin C. Hui, Peabody; Luis I. Victoriano, Danvers, both of Mass.

[73] Assignee: CVD Incorporated, Woburn, Mass.

[21] Appl. No.: 336,953

[22] Filed: Apr. 12, 1989

[51] Int. Cl.[4] ............................. C07F 5/00; C07F 5/06
[52] U.S. Cl. .......................................... 556/187; 556/1
[58] Field of Search ..................................... 556/1, 187

[56] References Cited

U.S. PATENT DOCUMENTS 4,720,561  1/1988  Bradley et al. ......................... 556/1

OTHER PUBLICATIONS

Gaines et al., "Inorg. Syn.", 15, (1974), pp. 203–207.

Primary Examiner—Paul F. Shaver
Attorney, Agent, or Firm—Wayne E. Nacker; Gerald K. White

[57] ABSTRACT

Waste material containing substantial amounts of $Li(MH_3R)$ compounds where M is Al or Ga are deactivated by dissolving and/or dispersing the waste material in a solvent in which ionic deactivation products are soluble and then adding a carbonyl-containing compound which reacts with the $Li(MH_3R)$ compound.

11 Claims, No Drawings

METHOD OF DEACTIVATING RESIDUES OF THE PRODUCTION OF DIMETHYLALUMINUM HYDRIDE AND DIMETHYLGALLIUM HYDRIDE

The present invention is directed to a method of deactivating pyrophoric and water-reactive residues of the production of dimethylaluminum hydride and dimethylgallium hydride.

BACKGROUND OF THE INVENTION

Waste materials which are pyrophoric, water-reactive, or both must be deactivated before they can be turned over to waste handlers for disposal. Of particular concern herein is waste products derived from the production of dimethylaluminum hydride ($Me_2AlH$) or dimethylgallium hydride ($Me_2GaH$). In particular, this invention is directed to deactivation of wastes containing compounds of the formula $Li(MH_3R)$ where M is Al or Ga and R is a low molecular weight hydrocarbon radical or a halogen.

One common method for deactivation of water-reactive substances is reaction with a weak proton donor, e.g., an alcohol, such as isopropanol. Reaction of $Li(MH_3R)$ compounds with weak proton donors produce gels which are difficult to handle, e.g., difficult to remove from their reaction vessels. Removal of deactivation products of $Li(MH_3R)$ compounds from reaction flasks is of significant concern because it is frequently necessary to deactivate such compounds directly in their reaction flasks. Although $Li(MH_3R)$ compounds are not necessarily pyrophoric, $Li(MH_3R)$-containing waste products often contain additional pyrophoric wastes which must be maintained under an inert atmosphere prior to deactivation.

It is known to produce dimethyl aluminum hydride by reaction of trimethyl aluminum with lithium aluminum hydride (LAH):

$$Al(CH_3)_3 + LiAlH_4 \rightarrow (CH_3)_2AlH + LiAlH_3CH_3.$$

or by a procedure described in U.S. patent application Ser. No. 07/136,032, which describes the reaction of waste products or residues of trimethylgallium production [$(CH_3)_2AlCl$, $(CH_3)_3Ga$ and $(CH_3)_3Al$] with lithium aluminum hydride to produce product dimethylaluminum hydride.

$$(CH_3)_2AlCl + LiAlH_4 \rightarrow (CH_3)_2AlH + LiAlH_3Cl$$

$$(CH_3)_3Ga + LiAlH_4 \rightarrow (CH_3)_2AlH + LiGaH_3CH_3$$

This application, in background, describes how the waste products of trimethylgallium production were deactivated either by reaction with ethyl alcohol or reaction with ethyl acetate in heptane.

The major waste product of the reaction of trimethylaluminum and LAH is lithiummethyltrihydridoaluminate ($LiAlH_3CH_3$), which is water reactive (though in itself not particularly pyrophoric). However, after distillation of product dimethylaluminum hydride, some dimethylaluminum hydride ($(CH_3)_2AlH$), which is pyrophoric, trimethylaluminum ($(CH_3)_3Al$), (TMA) which is also pyrophoric and LAH, which is not pyrophoric, remain. Deactivation of the major product, lithiummethyltrihydridoaluminate, is a major concern; however, the presence of the pyrophoric compounds requires that the major product be deactivated under an inert atmosphere, such as $N_2$. This generally requires that the deactivation take place in the reaction vessel itself. Naturally, it is highly desirable that the deactivation products be removable from the reaction vessel. Neither of the deactivation methods referenced in U.S. patent application 07/136,032 are suitable for the residues of the reaction of TMA and LAH. Isopropyl alcohol produces a gelled product. Reaction of the residues with ethyl acetate in heptane would produce insoluble products which could not easily be removed from the reaction flask.

If instead of reacting LAH with pure TMA, the LAH is reacted with the waste products of trimethyl gallium production, the major waste product is lithiumchlorotrihydroaluminate ($LiAlH_3Cl$) admixed with pyrophoric residual products. Similar deactivation problems are presented.

SUMMARY OF THE INVENTION

Pyrophoric waste products containing compounds of the fomrula $Li(MH_3R)$, where M is Al or Ga, are dissolved or suspended in a solvent which is selected to dissolve ionic deactivation products of the $Li(MH_3R)$ compounds. To the dissolved or suspended waste products is added a sufficient quantity of a carbonyl-containing organic compound in an amount sufficient to deactivate substantially all of the $Li(MH_3R)$ compound.

DETAILED DESCRIPTION OF CERTAIN PREFERRED EMBODIMENTS

The invention is directed to deactivation of pyrophoric wastes containing substantial amounts of i.e., 50% or more by weight, of compounds having the formula $Li(MH_3R)$ where M is Al or Ga and R is a halogen, such as chloride, fluorine, bromine or iodine, or a hydrocarbon radical having from 1 to 5 carbon atoms. The $Li(MH_3R)$ compound is water-reactive, but may in itself not be pyrophoric. The pyrophoric property of the waste, if not due to the $Li(MH_3R)$ compound itself, is afforded by other pyrophoric impurities. Because of the pyrophoric nature of these wastes, it is generally necessary to maintain the wastes under an inert, e.g., $N_2$, atmosphere until deactivation is effected.

As stated above, reaction of the pyrophoric waste with a weak proton donor, such as an alcohol, is generally unsatisfactory because the $Li(MH_3R)$ compound tends to form a gelled material when reacted directly with a hydroxyl group. Such gelled material may be difficult or impossible to remove from a reaction vessel.

In accordance with the invention, the waste material is dissolved and/or suspended in a solvent in which the deactivation products of the waste are soluble. Solubility of the deactivation products in the solvent facilitates removal of the deactivation products from the reaction vessel. The reaction of a $Li(MH_3R)$ product with a carbonyl compound is generally represented as follows:

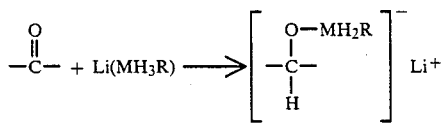

Thus, an ionic product is produced, requiring the solvent to be sufficiently polar to dissolve the ionic deactivation product or products. It is also required of a solvent that the solvent not be reactive with the $Li(MH_3R)$ compound. A reactive solvent would deactivate the Li(MH₃R) compound, but would react immediately and actively, making control of the reaction difficult.

Preferred solvents are ethers, which are sufficiently polar to dissolve the deactivation products. Ethers are also desirable in that they tend to complex the Li+ ions produced during deactivation. Although almost any liquid ether is a suitable solvent, higher molecular weight ethers, such as dibutyl ether (b.p. 142° C.), having relatively high boiling points are desirable from the standpoint of avoiding boiling during deactivation. The solvent should have a boiling point of above about 40° C., preferably about 50° C. or higher and more preferably about 100° C. or higher.

The solvent is added to the waste while the waste is maintained in an inert atmosphere. Mechanical means are generally employed to break up the waste into fine particles which dissolve in or become dispersed in the solvent. The volume of solvent added is generally at least about 5 times the volume of the waste material. A large volume of solvent relative to waste material both helps to ensure that the deactivation products are substantially dissolved and also helps to mediate heat produced by the exothermic deactivation reactions.

After the waste material is dissolved and/or dispersed in the solvent, the carbonyl-containing compound is added in a controlled manner so that deactivation proceeds without substantial refluxing of the solvent. Suitable carbonyl-containing compounds are aldehydes, ketones and esters, but not proton-donating compounds, such as carboxylic acids. The carbonyl-containing compound is added in at least about a stoichiometric amount relative to the Li(MH₃R) compound and preferably in a slight excess. For an aldehyde or ketone, the stoichiometric amount is one mole of carbonyl group per one mole of the Li(MH₃R) compound. For an ester, three moles of carbonyl are required to deactivate two moles of Li(MH₃R) compound.

After deactivation of the Li(MH₃R) compound, a small amount of pyrophoric waste material may remain, e.g., trialkylaluminum, trialkylgallium or dialkylaluminum hydride or dialkylgallium hydride. This remaining pyrophoric material may be deactivated by addition of a proton donor. For control of the further deactivation, it is preferred to utilize a weak proton donor, such as an alcohol.

After final deactivation, the dissolved deactivation products may be removed from the inert atmosphere and disposed of in an appropriate manner.

The following Example is a sample protocol for deactivation of waste product from the production of dimethylaluminum hydride from TMA and LAH.

EXAMPLE

A. Suspend Solid Residue in Butyl Ether

1. The reactive residue (approximately 1.3 kg of mostly LiAlH₃CH₃) is contained in a 12 liter stainless steel kettlehead reactor, and this is contained in a metal pan that can be used as oil bath.

2. Purge a 1 liter constant addition funnel and a dry ice condenser with nitrogen and fit them to the stainless flask. Also fit an air stirrer, but do not connect to motor.

3. Pressure siphon 6 liter of butyl ether (BUE) into the stainless flask. Alternatively, pour the ether into the addition funnel under nitrogen blanket, and let it stream into the flask. There is no exotherm or expansion at this stage.

4. Heat to 80° C. and after the solid mixture has softened, work the stirring shaft and paddle into the solid by gently turning the shaft back and forth by hand. Once the solid cake is broken down into pieces, the shaft may be connected to the motor and stirring may be started and maintained for half an hour before turning off the heat. Leave the stirrer on, and allow to cool to 35° C. It is very important that the suspension does not contain any chunks. Its aspect should be that of smooth, finely divided sand.

5. Set up a 22 liter flask into a metal pail and fit a dry ice condenser connected to a nitrogen line and bubbler, and air stirrer. Purge with nitrogen for 10 minutes or by two pump down-back fill cycles.

6. Construct a pressure siphoning transfer line with rubber stoppers, a straight piece of Teflon or glass and a length of Bev-a-line ®. Make sure that the bottom of the stainless flask is reached. The viscosity of the solution/suspension to be transferred is high, so use a wide tubing, e.g., 9 mm. The stirring shaft and paddle may now be removed from the stainless flask, and replaced by a stopper. Rinse the solid off the shaft and paddle with ethyl acetate (ETAC) from a squeeze bottle, then with isopropyl alcohol (IPA) and finally water. Pour the rinses, except for the water into a 5 gal. waste pail.

7. After connecting both flasks with the transfer tube, apply moderate pressure to make suspension flow. If this does not happen, slightly pressurize the system from the 22 liter flask and make sure that there is bubbling inside the stainless flask. This will ensure that the transfer tube is not blocked. Follow the same guidelines if the flow of waste into the 22 liter flask ceases.

8. Transfer 2 liters of fresh BUE to the stainless flask; hand-swirl and siphon to the 22 liter flask. Repeat the rinse with one liter of BUE. Remove the transfer tube, and deactivate as previously done with the stir shaft.

9. The stainless flask may now be opened to air, rinsed successively with ETAC, IPA and water and allowed to air out.

B. Add ETAC

1. The 22 liter flask contains 1.3 kg of material dissolved in a total of 9 liters BUE. Purge a 1 liter constant addition funnel with nitrogen. Fill it to the mark with ETAC 99% (suggest ALFA #11950 or 13802) and fit it to the 22 liter flask.

2. Hand-start the stirrer and slowly build up speed to keep the suspension well stirred. Surround the flask and fill the condenser with dry ice.

3. Start the addition of ETAC at an approximate rate of 1 drop/second. There will be an exotherm and some expansion as shown by an increase in the rate of bubbling.

4. Some heating will be observed. This is part of the procedure. The lowest boiler in the mixture is ETAC (77° C.), so an operating temperature of 60° C. is safe. In this part of the procedure there is no evolution of gas.

5. After addition of the first liter of ETAC is completed (some 5 hours), the rate of addition may be increased to 2 drops/second. A further two liters must be added. The funnel may be charged with ETAC from the top under slight positive pressure of nitrogen. WARNING: If a large excess of LAH was used in the preparation of DMAH, or if the yield of crude product was worse than 80%, there may be need for additional ETAC. In order to check this possibility, allow to cool to room temperature, and rapidly add approximately 100 ml. of ETAC. If there is any heating, additional reagent is necessary.

6. The 22 liter flask now contains a solution-suspension of lithium methyltriethoxyaluminate.

$$2LiMeAlH_3 + 3CH_3COOC_2H_5 \rightarrow 2LiMeAl(OC_2H_5)_3$$

C. Add IPA

1. The addition funnel is now charged with IPA and deactivation proceeds as for other waste. The material is not very reactive and the rate of addition should not exceed two drops/second in order to avoid accumulation of unreacted IPA. If stirring is inefficient, there is the possibility of formation of a hard crust of solid on top. Should this happen, stop the addition of IPA and stirring, disconnect the stir motor and work the shaft up, down and around in order to break the layer of solids.

2. If the preparation of dimethyl aluminum hydride (DMAH) was done in the scale of 0.8 kg. LAH and 1.4 kg. TMA, there should be 2.5 liters of IPA spent in the deactivation, provided the yield of crude product was 80% or better.

3. The absence of bubbling upon addition of fresh IPA is taken as an indication of full deactivation. No water should be added to the flask as the contents coagulate into a solid mass impossible to pour out.

4. Fill two 5 gal. plastic waste pails approximately one-third with crushed ice and pour the waste into them. The flask may now be rinsed with fresh BUE, acetone and water. All three rinses must be poured into the waste pails.

While the invention has been described in terms of certain preferred embodiments, modifications obvious to one with ordinary skill in the art may be made without departing from the scope of the invention.

Various features of the invention are set forth in the following claims.

What is claimed is:

1. A method of deactivating a pyrophoric waste material containing a substantial amount of a compound of the formula Li(MH$_3$R), wherein M is Al or Ga and R is a halogen or an alkyl moiety containing from 1–5 carbons, the method comprising:
   dissolving or dispersing said waste in a non-reactive solvent selected to be of sufficient polarity to dissolve ionic deactivation products of said Li(MH$_3$R) compound, and
   reacting said waste with a non-proton-donor, carbonyl-containing compound in at least a stoichiometric amount relative to said Li(MH$_3$R) compound.

2. A method according to claim 1 wherein said solvent has a boiling point of at least about 40° C.

3. A method according to claim 1 wherein said solvent has a boiling point of at least about 50° C.

4. A method according to claim 1 wherein said solvent has a boiling point of at least about 100° C.

5. A method according to claim 1 wherein said solvent is an ether.

6. A method according to claim 5 wherein said ether has a boiling point of at least about 40° C.

7. A method according to claim 5 wherein said ether has a boiling point of at least about 50° C.

8. A method according to claim 5 wherein said ether has a boiling point of at least about 100° C.

9. A method according to claim 1 wherein said solvent is dibutyl ether.

10. A method according to claim 1 further adding a proton donor to the reacted waste to deactivate residual pyrophoric compounds in said waste material.

11. A method according to claim 10 wherein said proton donor added to said reacted waste material is an alcohol.

* * * * *